(12) United States Patent
Welch

(10) Patent No.: US 6,255,322 B1
(45) Date of Patent: Jul. 3, 2001

(54) 2-(4-HYDROXYPIPERIDINO)-1-ALKANOL DERIVATIVES AS ANTIISCHEMIC AGENTS

(75) Inventor: Willard McKowan Welch, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 08/178,269

(22) PCT Filed: Jun. 19, 1992

(86) PCT No.: PCT/US92/04973

§ 371 Date: Jan. 13, 1994

§ 102(e) Date: Jan. 13, 1994

(51) Int. Cl.[7] .................. A61K 31/445; C07D 215/22
(52) U.S. Cl. ................ 514/312; 514/260; 514/322; 514/323; 544/292; 546/153; 546/199; 546/201
(58) Field of Search ................... 546/153, 199, 546/201, 216; 544/292; 514/260, 312, 322, 323

(56) References Cited

U.S. PATENT DOCUMENTS

| | | | |
|---|---|---|---|
| 3,294,804 | 12/1966 | Carabateas et al. | 546/240 |
| 3,509,164 | 4/1970 | Caron et al. | 546/240 |
| 4,248,877 | * 2/1981 | Rissi | 546/221 |
| 4,529,730 | * 7/1985 | Schneider | 546/205 |
| 5,034,401 | * 7/1991 | Frost | 514/323 |
| 5,112,821 | * 5/1992 | Harrison | 546/114 |
| 5,185,343 | * 2/1993 | Chenard | 514/298 |
| 5,212,181 | * 5/1993 | Frost | 514/312 |

FOREIGN PATENT DOCUMENTS

| | | | |
|---|---|---|---|
| 351282 | 1/1990 | (EP) . | |
| 398578 | 11/1990 | (EP) . | |
| 2546166 | 3/1983 | (FR) . | |
| 2071094 | 9/1981 | (GB) | C07D/401/00 |
| 9117156 | 11/1991 | (WO) | C07D/401/06 |

OTHER PUBLICATIONS

Schoepp et al., J. Neural. Transm. [Gen. Sect.] (1991) 85:131–143.

J. Lehmann, Drugs of the Future, vol. 14, No. 11, 1989, 1059–1071.

D. Lodge and D. Schoepp, Excitatory amino acid receptors (Chart), 1993, Receptor Nomenclature Supplement, Elsevier Trends Journals, Elsevier Science Publishers Ltd. (UK).

Carron et al., Drug Res., V. 21, pp. 1992–1999 (1971).

Gotti et al., J. Pharm. Exp. Therap., V. 247, pp. 1211–1221 (1988).

Carter et al., J. Pharm. Exp. Therap., V. 247, pp. 1222–1232 (1988).

Muro et al "Piperazinyl or piperadinyl derivatives" CA 89: 43498y (1978).

Muro et al "Aminoalcohol derivatives" CA 89: 146938 w (1978).

* cited by examiner

Primary Examiner—Ceila Chang
(74) Attorney, Agent, or Firm—Peter C. Richardson; Gregg C. Benson; Todd M. Crissey

(57) ABSTRACT

A series of 2-(4-hydroxypiperidino)-1-alkanol derivatives are useful as medicaments for the treatment of traumatic injuries to the brain and spinal cord and neuronal degenerative diseases including senile dementias, in mammals, especially humans.

12 Claims, No Drawings

2-(4-HYDROXYPIPERIDINO)-1-ALKANOL DERIVATIVES AS ANTIISCHEMIC AGENTS

CROSS REFERENCE TO RELATED APPLICATIONS

This application is a § 371 application of PCT/US92/04973, filed Jun. 19, 1992, which claims priority of U.S. patent application 07/731,577, filed Jul. 17, 1991, now abandoned.

BACKGROUND OF THE INVENTION

The present invention is directed to neuroprotective (antiischemic excitatory amino acid receptor blocking) 2-(4-hydroxypiperidino)-1-alkanol derivatives defined by formula (I) below; pharmaceutically acceptable salts thereof; a method of using these compounds in the treatment of stroke, traumatic injury to the brain and spinal cord, and neuronal degenerative diseases including (but not limited to) senile dementias such as Alzheimer's disease, Huntington's disease and Parkinson's disease in mammals, especially humans; and to certain intermediates therefor.

Ifenprodil (A) is a racemic, so-called dl-erythro compound having the relative stereochemical formula

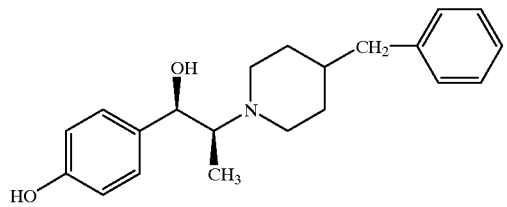

(A)

which is marketed as a hypotensive agent, a utility shared by a number of close analogs. Carron et al., U.S. Pat. No. 3,509,164; Carron et al., Drug Res., v. 21, pp. 1992–1999 (1971). More recently, ifenprodil has been shown to possess antiischemic and excitatory amino acid receptor blocking activity. Gotti et al., J. Pharm. Exp. Therap., v. 247, pp. 1211–21 (1988); Carter et al., loc. cit., pp. 1222–32 (1988).

See also French Patent 2546166 and EPO publication EP-A1-351282, published Jan. 17, 1990. A goal, substantially met by the present invention, has been to find compounds possessing neuroprotective activity in good measure, while at the same time having lowered or no significant hypotensive effect.

Certain 1-phenyl-3-(4-aryl-4-acyloxy-piperidino)-1-propanols have also been reported to be useful as analgesics, U.S. Pat. No. 3,294,804; 1-[4-(amino- and hydroxy-alkyl)phenyl]-2-(hydroxy-4-tolylpiperazino)-1-alkanols and alkanones have been reported to possess analgesic, antihypertensive, psycho-tropic or antiinflamatory activity, Japanese Kokai 53-02,474 (CA 89:43498y; Derwent Abs. 14858A) and 53-59,675 (CA 89:146938w; Derwent Abs. 48671A); and 2-piperidino-1-alkanol derivatives have been reported to be active as antiischemics, EP 398,578-A and Der 90-350,327/47.

SUMMARY OF THE INVENTION

The present invention is directed to compounds of the formula

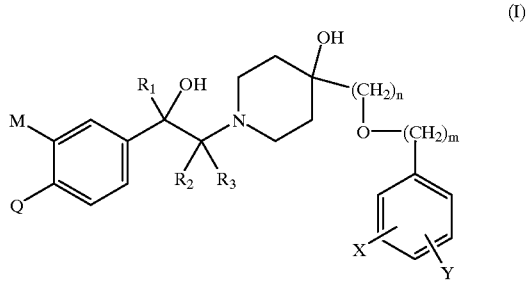

(I)

wherein $R_1$, $R_2$ and $R_3$ are each selected from the group consisting of hydrogen, alkyl having 1 to 6 carbons, phenyl and substituted phenyl, wherein the substituent on said substituted phenyl is selected from the group consisting of hydroxy, alkyl having 1 to 4 carbons, chloro, bromo, fluoro, trifluoromethyl, amino, nitro and alkoxy having 1 to 4 carbons;

or $R_1$ and $R_2$ when taken together form a methylene, ethylene, propylene or butylene group;

m is 0 to 2;

n is 1 or 2;

X and Y are each selected from the group consisting of hydrogen, chloro, bromo, fluoro, trifluoromethyl, alkoxy having 1 to 4 carbons, alkyl having 1 to 4 carbons, hydroxy, amino, nitro and substituted phenoxy, wherein the substituent on said substituted phenoxy is selected from the group consisting of hydrogen, hydroxy, alkyl having 1 to 4 carbons, chloro, bromo, fluoro, trifluoromethyl, nitro, amino and alkoxy having 1 to 4 carbons;

M and Q are each selected from the group consisting of hydrogen, hydroxy, amino, chloro, bromo, fluoro, trifluoromethyl, nitro, alkyl having 1 to 4 carbons, alkoxy having 1 to 4 carbons, N,N-dialkylamino having 1 to 4 carbons in each of said alkyls, N-alkylamino having 1 to 4 carbons, $NHCOR_4$, $NHCOOR_5$ and $NHSO_2R_6$;

wherein $R_4$ is selected from the group consisting of hydrogen, alkyl having 1 to 6 carbons, phenyl and substituted phenyl, wherein the substituent on said substituted phenyl is selected from the group consisting of hydroxy, chloro, bromo, fluoro, trifluoromethyl, amino, nitro, alkyl having 1 to 4 carbons and alkoxy having 1 to 4 carbons;

and wherein $R_5$ and $R_6$ are each selected from the group consisting of alkyl having 1 to 6 carbons, phenyl and substituted phenyl, wherein the substituent on said substituted phenyl is selected from the group consisting of hydroxy, chloro, bromo, fluoro, trifluoromethyl, amino, nitro, alkyl having 1 to 4 carbons and alkoxy having 1 to 4 carbons;

or M and Q when taken together form a divalent radical Z, wherein Z is selected from the group consisting of

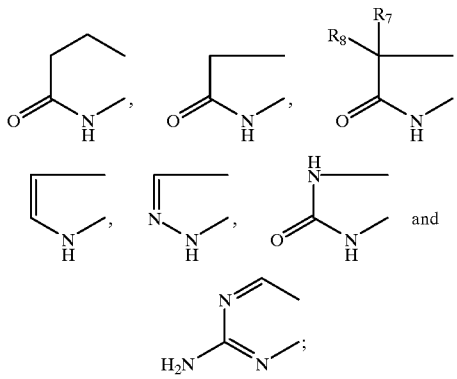

wherein $R_7$ and $R_8$ are each selected from the group consisting of hydrogen and methyl;

and the pharmaceutically acceptable acid addition salts of these compounds.

The expression "pharmaceutically acceptable acid addition salts" is intended to include but is not limited to such salts as the hydrochloride, hydrobromide, hydroiodide, nitrate, hydrogen sulfate, dihydrogen phosphate, mesylate, maleate, and succinate. Such salts are conventionally prepared by reacting the free base form of the compound (I) with an appropriate acid, usually one molar equivalent, and in a solvent. Those salts which do not precipitate directly are generally isolated by evaporation of the solvent and/or addition of a non-solvent followed by filtration.

A preferred group of compounds of the present invention are those in which N and Q form a radical Z, wherein Z is

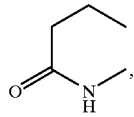

$R_1$ and $R_2$ are hydrogen and $R_3$ is methyl and the compounds possess 1r*, 2s* or erythro relative stereochemistry at the 1- and 2-positions of the propanol chain, i.e.,

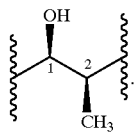

A second preferred group of compounds of this invention are those in which N and Q form a radical Z, wherein Z is

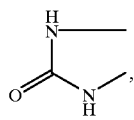

$R_1$ and $R_2$ are hydrogen and $R_3$ is methyl and the compounds possess 1s*, 2s* or threo relative stereochemistry at the 1- and 2- positions of the propanol chain, i.e.,

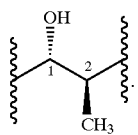

The present invention is also directed to pharmaceutical compositions containing a compound of the invention of formula I, and to methods of treating a mammal, particularly human subject, suffering from a central nervous disorder, which comprises administering to said mammal a neuroprotective effective amount of a compound of the formula (I). Said compositions and methods are particularly valuable in the treatment of traumatic injury to the brain and spinal cord, stroke, Alzheimer's disease, Parkinson's disease, Huntington's disease and related disorders of the central nervous system.

The present invention is further directed to intermediate compounds of the formula

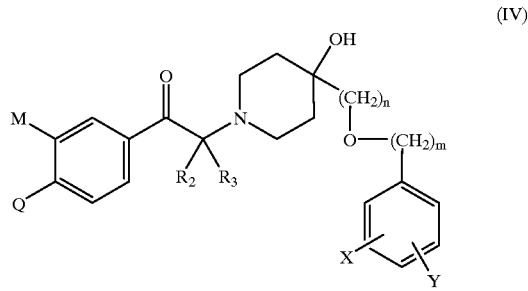

(IV)

wherein
$R_2$ and $R_3$ are each selected from the group consisting of hydrogen, alkyl having 1 to 6 carbons, phenyl and substituted phenyl, wherein the substituent on said substituted phenyl is selected from the group consisting of hydroxy, alkyl having 1 to 4 carbons, chloro, bromo, fluoro, trifluoromethyl, amino, nitro and alkoxy having 1 to 4 carbons;

m is 0 to 2;

n is 1 or 2;

X and Y are each selected from the group consisting of hydrogen, chloro, bromo, fluoro, trifluoromethyl, alkoxy having 1 to 4 carbons, alkyl having 1 to 4 carbons, hydroxy, amino, nitro and substituted phenoxy, wherein the substituent on said substituted phenoxy is selected from the group consisting of hydrogen, hydroxy, alkyl having 1 to 4 carbons, chloro, bromo, fluoro, trifluoromethyl, nitro, amino and alkoxy having 1 to 4 carbons;

M and Q are each selected from the group consisting of hydrogen, hydroxy, amino, chloro, bromo, fluoro, trifluoromethyl, nitro, alkyl having 1 to 4 carbons, alkoxy having 1 to 4 carbons, N,N-dialkylamino having 1 to 4 carbons in each of said alkyls, N-alkylamino having 1 to 4 carbons, NHCOR$_4$, NHCOOR$_5$ and NHSO$_2$R$_6$;

wherein R$_4$ is each selected from the group consisting of hydrogen, alkyl having 1 to 6 carbons, phenyl and substituted phenyl, wherein the substituent on said substituted phenyl is selected from the group consisting of hydroxy, chloro, brono, fluoro, trifluoromethyl, amino, nitro, alkyl having 1 to 4 carbons and alkoxy having 1 to 4 carbons;

and wherein $R_5$ and $R_6$ are each selected from the group consisting of alkyl having 1 to 6 carbons, phenyl and substituted phenyl, wherein the substituent on said substituted phenyl is selected from the group consisting of hydroxy, chloro, bromo, fluoro, trifluoromethyl, amino, nitro, alkyl having 1 to 4 carbons and alkoxy having 1 to 4 carbons;

or N and Q when taken together form a divalent radical Z, wherein Z is selected from the group consisting of

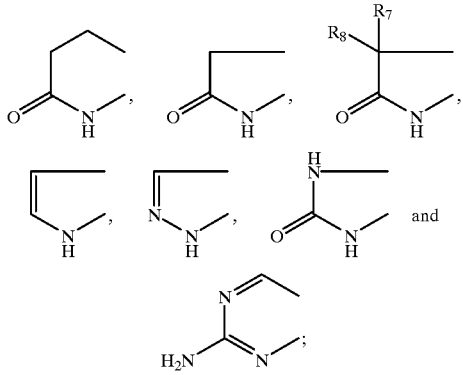

and wherein $R_7$ and $R_8$ are each selected from the group consisting of hydrogen and methyl.

Depending on the precise values of $R_1$, $R_2$ and $R_3$, the compounds of formula (I) can have one or two asymmetric centers, and can therefore exist in various isomeric forms. All such isomers are within the scope of this invention. The individual isomers can be separated by classical methods well-known to those skilled in the art.

DETAILED DESCRIPTION OF THE INVENTION

The compounds of the present invention, having the formula (I) defined above, are readily and generally prepared by reaction of chloro compound (II) with piperidine (III), followed by reduction of the resulting ketone (IV) to an alcohol as detailed below.

The precursor ketones are generally initially prepared with —OH and —NH$_2$ substituent groups in protected form, i.e., as —OA$_1$, or —NHA$_2$ groups in the compounds of formula (IV). A$_1$ and A$_2$ are defined below. Such protected ketones are generally formed by reacting an appropriately substituted 2-halo-1-alkanone (II) with an appropriately substituted piperidino derivative (III), e.g.,

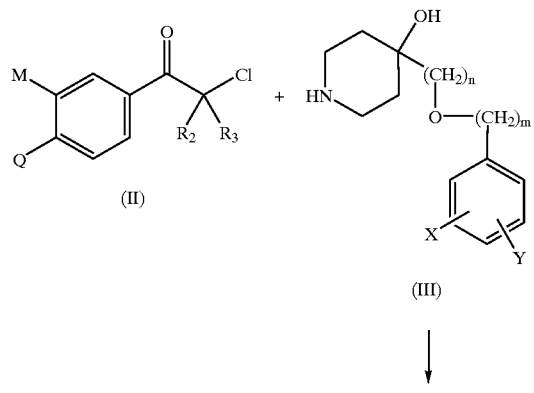

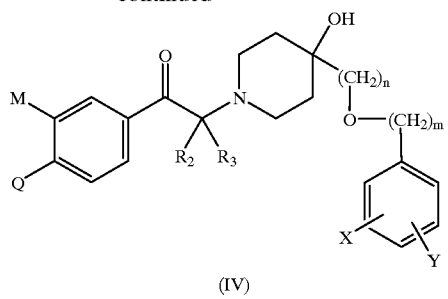

(IV)

Reaction of compound (II) with compound (III) is carried out under conditions typical of nucleophilic displacements in general. Where the two reactants are about equivalent in availability, close to substantially molar equivalents may be used; although when one is more readily available, it is usually preferred to use that one in excess, in order to force this bimolecular reaction to completion in a shorter period of time. The reaction is generally carried out in the presence of at least 1 molar equivalent of a base, the piperidine derivative itself, if it is readily available, but more usually a tertiary amine which is at least comparable in base strength to the nucleophilic piperidine; and in a reaction inert solvent such as ethanol. If desired, the reaction is catalyzed by the addition of up to one molar equivalent or more of an iodide salt (e.g., NaI, KI). Temperature is not critical, but will generally be somewhat elevated in order to force the reaction to completion within a shorter time period, but not so high as to lead to undue decomposition. A temperature in the range of 50–120° C. is generally satisfactory. Conveniently, the temperature is the reflux temperature of the reaction mixture.

As used in the preceding paragraph, and elsewhere herein, the expression "reaction inert solvent" refers to any solvent which does not interact with starting materials, reagents, intermediates or products in a manner which adversely affects the yield of the desired product.

If desired, those ketone intermediates (IV) having OH or NH$_2$ groups in protected form (OA$_1$ or NHA$_2$), can be deprotected at this stage by conventional methods.

For example when A$_1$ is triisopropylsilyl or tertbutyldimethylsilyl, the protecting group is conveniently removed by reaction with tetrabutylammonium fluoride (generally, substantially 2 molar equivalents) in a reaction inert solvent such as tetrahydrofuran. When A$_1$ is benzyl or A$_2$ is benzyloxycarbonyl, the protecting group will generally be removed by conventional hydrogenolysis over a noble metal catalyst in a reaction inert solvent, e.g., using 10% Pd/C as catalyst, preferable at low pressures (e.g., 1–10 atmospheres) and temperatures (e.g., 20–750° C.) and generally in a reaction inert solvent such as methanol.

Generally, the ketone intermediates (IV) are conveniently converted to corresponding alcohols by one of two conventional reduction methods, to selectively produce either the threo compounds or the erythro compounds of formula (I).

As used in the preceding paragraph, and elsewhere herein, the term "threo" or 1r*, 2s* refers to the relative stereochemistry at the 1- and 2- positions of the propanol chain, i.e.,

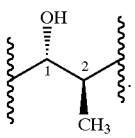

and the term "erythro" or 1r*, 2s* refers to the relative stereochemistry at the 1- and 2-positions of the propanol chain, i.e.,

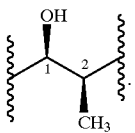

To obtain the desired erythro compounds of formula (I) the corresponding ketone intermediates (IV) are conveniently reduced with potassium borohydride, usually in excess (e.g. greater than 5 mole equivalents), in the presence of glacial acetic acid in a protic solvent such as ethanol, generally at a temperature range of 15–250° C.

To obtain the desired threo compounds of formula (I) the corresponding ketone intermediates (IV) are conveniently reduced with sodium borohydride, usually in excess (e.g. greater than 5 mole equivalents), in a protic solvent such as ethanol, generally at a temperature range of 15–25° C. The resulting reaction mixture is chromatographed on a silica gel column to obtain the said threo compounds of formula (I).

Any protecting groups which are still in place after ketone reduction are then removed according to standard methods described above.

The starting materials and reagents required for the synthesis of the compounds of the present invention are readily available, either commercially, according to literature methods, or by methods exemplified in Preparations below.

The present compounds of the formula (I) possess selective neuroprotective activity, based upon their antiischemic activity and ability to block excitatory amino acid receptors, while at the same time having lowered or no significant hypotensive activity. The antiischemic activity of the present compounds is determined according to one or more of the methods which have been detailed previously by Gotti et al. and Carter et al. cited above, or by similar methods.

The ability of the compounds of the present invention to block excitatory amino acid receptors is demonstrated by the drugs ability to rescue fetal rat neurons in culture which have been exposed to the excitotoxic amino acid glutamate. The following is a typical procedure.

Part I: Cell Isolation:

Embryos at 17 days gestation are removed from rats and placed into Tyrode's solution. The brainsiare then removed and placed into fresh Tyrode's solution. Using fine iris knives, the hindbrain and thalamus are removed. The forebrain is then separated into two hemispheres. Next, the meninges are removed gently. The hippocampus appears as a darkened folded area on the inner side of the cortex edge. The hippocampus is carefully cut away from the rest of the tissue and placed in a separate corner of the dish. When all of the dissection is completed, the hippocampal tissue reserved in the corner is minced into 1 mm pieces. These pieces are removed, using a Pasteur pipette and placed into a sterile tube. The Tyrode's solution is aspirated off gently and Calcium-Magnesium Free Tyrode's solution is added. The tissue is washed 3 times with Calcium-Magnesium Free Tyrode's solution. This final wash is incubated 15 minutes at 37 degrees Centigrade. The buffer is again removed and replaced with 1 ml fresh Calcium-Magnesium Free Tyrode's solution. Trypsin is now added at 0.1% (100 µl of a 10 mg/ml stock sterile solution). The tube is incubated for 1 hour at 37 degrees Centigrade. After trypsin incubation the tissue is washed with serum containing medium in order to stop the action of the trypsin. The tissue is resuspended in 1 ml of fresh medium and triturated with a fine bore Pasteur pipette.

Cells are then counted using a hemocytometer. Cells are then seeded onto a 96-well Falcon Primeria tissue culture plates at 75000 cells per well in complete medium. Complete medium is composed of Minimal Essential Medium (MEN) with Earle's salts, 10% Fetal Calf Serum (Hyclone), 10% Equine Serum, L-glutamine (2 mM), Penicillin-Streptomycin (100 U per ml) and Glucose (to make the final concentration 21 mM a 100× stock containing 27.8 g per 100 ml is prepared). The plates are fed on day 3 with fresh medium. Then on day 6 cytosine arabinoside at 10 µm is added to the cultures with fresh medium. Then two days later the cytosine arabinoside is removed and replaced with Maintenance medium, which is complete medium minus the Fetal Calf Serum. The plates are then fed twice a week. Three weeks from the time of dissection the plates are used in the glutamate toxicity experiments, in order to insure proper development of the neurons in culture.

Part 2: Glutamate Treatment and Post-Glutamate Drug Addition:

After three weeks in culture, the medium is removed from the cells and the cells are washed three times in chloride free controlled salt solution (CSS-Cl). CSS-Cl contains 69 mM $Na_2SO_4$, 2.67 mM $K_2SO_4$, 0.33 mM $NaHPO_4$, 0.44 mM $KH_2PO_4$, 1 mM $NaHCO_3$, 1 mM $MgSO_4$, 10 mM HEPES (N-2-hydroxyethylpiperazine-$N^1$-2-ethanesulfonic acid), 22.2 mM glucose, and 71 ml sucrose at pH 7.4. After washing, glutamate is added at 1 to 3 mM in CSS-Cl buffer with appropriate control wells containing buffer without glutamate. The plates are incubated at 37 degrees celsius for 15 to 20 minutes. Following glutamate incubation, the plates are washed with serum free medium twice. The test drugs are prepared at the appropriate concentrations in serum free medium and added to the corresponding wells of the microtiter plate (100 µl per well). Negative control wells receive serum free medium with no drug. Several glutamate treated wells are also given serum free medium with no drug to serve as positive controls. The plate is incubated overnight at 37 degrees celsius and the following day viability is assessed using the LDH (lactate dehydrogenase) and MTT (methyl thiotetrazolinium) assays.

Part 3: Assessment of Cell Viability:

The 100 µl of medium from each plate is removed and transferred to a clean plate to be assayed for the amount of LDH released. Then 100 µl per well of MTT solution is added. This MTT solution is prepared by adding 10 µl of MTT stock (5 mg/ml in PBS, phosphate buffered saline) for every 100 µl serum free medium. Plates are incubated at 37 degrees for 4 to 6 hours. Then 100 µl of acid-alcohol solution (0.08 N HCl in isopropanol) is added to each well and the wells were mixed vigorously in order to dissolve the purple crystals. Control wells should contain medium with MTT and acid-alcohol, but no cells. The plates are then read on a microplate reader, using a dual wavelength setting test filter at 570 nm and reference filter at 630 nm. The plates must be read within 1 hour.

The medium which is removed is then assayed for LDH. Equal volumes of the samples removed are added to LDH reaction mixture. In this case appropriate wells are pooled to make 500 µl samples. For each sample, reaction mixture is prepared by mixing 480 µl of 0.1 M sodium phosphate buffer, pH 7.5, 10 µl of sodium pyruvate (66 mN) and 10 µl NADH reduced (each vial of NADH containing 5 mg is reconstituted in 440 µl 0.1 N NaOH and 10 µl of this is used per sample). The sample is quickly added to the reaction mixture in cuvettes and the disappearance of absorbance at 340 nm is measured on a Beckman DU-8 spectrophotometer.

Undesired hypotensive activity is also determined by known methods, for example, according to the methods of Carron et al, also cited above.

Such selective neuroprotective antiischemic and excitatory amino acid blocking activities make the compounds of the present invention useful in the treatment of traumatic injury to the brain and spinal cord, degenerative CNS (central nervous system) disorders such as stroke, Alzheimer's disease, Parkinson's disease and Huntington's disease, without significant potential for concurrent undue drop in blood pressure. In the systemic treatment of such diseases in a human subject with a neuroprotective amount of compounds of the formula (I), the dosage is typically from about 0.02 to 10 mg/kg/day (1–500 mg/day in a typical human weighing 50 kg) in single or divided doses, regardless of the route of administration. Of course, depending upon the exact compound and the exact nature of the individual illness, doses outside this range may be prescribed by the attending physician. The oral route of administration is generally preferred. However, if the patient is unable to swallow, or oral absorption is otherwise impaired, the preferred route of administration will be parenteral (i.m., i.v.) or topical.

The compounds of the present invention are generally administered in the form of pharmaceutical compositions comprising at least one of the compounds of the formula (I), together with a pharmaceutically acceptable vehicle or diluent in a ratio of 1:20 to 20:1 respectively. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like, and for topical administration, in the form of solutions, lotions. ointments, salves and the like.

The present invention is illustrated by the following examples, but is not limited to the details thereof.

All non-aqueous reactions were run under dry, oxygen free nitrogen for convenience and generally to maximize yields. All solvents/diluents were dried according to standard published procedures or purchased in a predried form. All reactions were stirred either magnetically or mechanically. NMR spectra are recorded at 300 MHz and are reported in ppm downfield from trimethylsilane. The NMR solvent was $CDCl_3$ unless otherwise specified. IR spectra are reported in micrometers, generally specifying only strong signals.

EXAMPLE 1

(±)-3,4-Dihydro-6-(1-hydroxy-2-(1-(4-hydroxy-4-phenoxy-methyl)piperidinyl)ethyl)quinoline-2-(1H)-one A mixture of 300 mg (1.23 mol) of 4-hydroxy-4-(phenoxy-methyl)piperidine hydrochloride, 409 mg (1.84 mmol) of 6-(2-chloroacetyl)-3,4-dihydroquinolin-2-(1H)-one and 0.514 mL (0.373 g, 3.7 mmol) of triethylamine in 25 mL of acetonitrile was heated at 60° C. overnight. The solvent was then removed in vacuo and the residues partitioned between water and ethyl acetate and the organic layer was washed again with water and with brine. The ethyl acetate layer was dried with brine and magnesium sulfate and the solvent was evaporated to give 3,4-dihydro-6-(1-oxo-2-(1-(4-hydroxy-4-phenoxymethyl)piperidinyl)ethyl) quinoline-2-(1H)-one as a brown solid which was used in the subsequent reduction step without further purification.

The above ketone was dissolved in 25 mL of absolute ethanol and 500 mg (13.1 mmol) of $NaBH_4$ was added portionwise over 20 min. The reaction mixture was stirred at room temperature for 4 hrs. and then the solvent was removed and the residues were partitioned between water and ethyl acetate. After drying, the ethyl acetate was removed in vacuo and the residue was chromatographed on silica gel to give the product, 73 mg (15%), m.p. 186–188° C. NMR ($CD_3OD$) δ 1.70–2.10 (4H, m), 2.52–3.07 (10H, m), 3.33 (2H, s), 3.83 (2H, s), 6.82–7.38 (8H, m).

EXAMPLE 2

(±)-5-(1-Hydroxy-2-(1-(4-hydroxy-4-phenoxymethyl)-piperidinyl)ethyl)benzimidazolin-2-one Following the procedure of Example 1, the present title compound was obtained from 4-hydroxy-4-(phenoxymethyl)piperidine hydrochloride (1.23 mmol), 5-(2-chloroacetyl)-2-hydroxybenzimidazole (1.84 mmol) and triethylamine (3.7 mmol) in 25 ml of acetonitrile. The resulting ketone was stirred with sodium borohydride (13.1 mmol) in absolute ethanol to yield the desired compound after chromatography on silica gel. Yield 35%, m.p. 232–235° C.

Anal. Calcd. for $C_{21}H_{25}N_3O_4 \cdot H_2O$: C, 62.81; H, 6.77; N. 10.46. Found: C, 62.98; H, 6.54; N, 10.32.

EXAMPLE 3

(±)-5-(1-Hydroxy-2-(1-(4-hydroxy-4-phenoxymethyl)-piperidinyl)ethyl-2-oxindole

Following the procedure of Example 1, the present title compound was obtained from 4-hydroxy-4-(phenoxymethyl)piperidine hydrochloride (1.23 mmol), 5-(2-chloroacetyl)oxindole (1.84 mmol) and triethylamine (3.7 mmol) in 25 ml of acetonitrile. The resulting ketone was stirred with sodium borohydride (13.1 mmol) in absolute ethanol to yield the desired compound after chromatography on silica gel. Yield 40%, m.p. 171–174° C.

EXAMPLE 4

(±)-Erythro-5-(1-hydroxy-2-(1-(4-hydroxy-4-phenoxymethyl)piperidinyl)propyl)benzimidazolin-2-one A solution of 933 mg (2.36 mol) of (±)-1-(5-(2-hydroxybenzimidazolyl))-2-(1-(4-hydroxy-4-phenoxymethyl) piperidinyl)propan-1-one in 10 mL of glacial acetic acid and 50 mL of absolute ethanol was treated portionwise with 944 mg (17.48 mol) of potassium borohydride between 15–20° C. and the resulting solution was stirred overnight at room temperature. The reaction mixture was then evaporated to dryness and the residues taken up in minimal water. The pH of this solution was adjusted to 7–8 with solid $NaHCO_3$. precipitating a solid. This material was insoluble in chloroform and relatively insoluble in ethyl acetate. The whole was again evaporated to dryness and the residues, which had crystallized, were taken up in ethanol and filtered to remove salts. The ethanol was evaporated and the residue taken up in isopropanol and treated with HCl gas in ether to precipitate a non-crystalline salt which was separated by filtration and dried in a stream of dry nitrogen. This material was dissolved in hot ethyl acetate with methanol and clarified with decolorizing charcoal and then the methanol was boiled off. Cooling gave a colorless crystalline product, 410 mg (40%), m.p. 254–255° C. IR (KBr) 5.90 $\mu$m; NMR (CD$_3$OD) $\delta$ 1.22 (3H, d, J=7), 1.95–2.09 (2H, m), 2.15–2.30 (2H, m), 3.42–3.76 (4H, m), 3.91 (2H, s), 5.47 (1H, s), 6.92–7.35 (8H, m).

EXAMPLE 5

(±)-Threo-5-(1-hydroxy-2-(1-(4-hydroxy-4-phenoxymethyl)-piperidinyl)propyl)benzimidazolin-2-one A total of 700 mg (18.4 mol) of sodium borohydride was added portionwise to a suspension of 325 mg (0.82 mmol) of (±)-1-(5-(2-hydroxybenzimidazolyl)-2-(1-(4-hydroxy-4-phenoxymethyl)piperidinyl)propan-1-one in 20 mL of absolute ethanol and the reaction mixture was stirred overnight at room temp. The solvent was then evaporated and the residual foam was taken up between ethyl acetate and water and the aqueous layer was extracted with ethyl acetate. The combined ethyl acetate extracts were dried and evaporated and the residual foam was chromatographed on silica gel using 1:1 ethanol/ethyl acetate to give the product as a white solid, m.p.>250° C. NMR (Acetone-d$_6$) $\delta$ 0.79 (3H, d, J=7), 1.71–1.88 (2H, m), 11.90–2.08 (2H, m), 2.48–2.88 (4H, m), 3.01 (1H, t, J=7), 3.88 (2H, s), 4.26 (1H, d, J=7), 6.86–7.32 (8H, m);

Anal. Calcd for C$_{22}$H$_{27}$N$_3$O$_4$.1.5 H$_2$O:C, 62.24; H, 7.12; N, 9.89. Found: C, 61.72; H, 6.73; N, 9.03.

EXAMPLE 6

(±)-Erythro-3,4-dihydro-6-(1-hydroxy-2-(1-(4-hydroxy-4-phenoxymethyl)piperidinyl)propyl)quinolin-2 (1H)one A solution of 7.13 g (17.5 mmol) of (±)-1-(6-(1,2,3,4-etrahydro-2-oxoquinolinyl))-2-(1-(4-hydroxy-4-phenoxymethyl)piperidinyl)propan-1-one in 135 mL of absolute ethanol and 70 mL of glacial acetic acid was treated portionwise with 6.22 g (115 mmol) of KBH$_4$ at 15–20° C. and was then allowed to warm to room temperature for 30 min. The reaction mixture was evaporated to dryness and the residue was taken up in ice and cold water and this was basified with solid NaHCO$_3$. The solid which precipitated was separated by filtration, washed with water and air dried to give 3.66 g of crystalline free base, m.p. 192–196° C. The filtrate was extracted with ethyl acetate and the combined extracts were dried with brine and with MgSO$_4$ and evaporated to give an additional 786 mg of product (total yield 62%). A 510 mg sample of this material was dissolved in ethyl acetate and treated with a solution of HCl gas in ether to give 475 mg of the crystalline hydrochloride salt, m.p. 214–216° C. (dec). IR (KBr) $\mu$m; NMR (CD$_3$OD) $\delta$ 1.15 (3H, d, J=7), 1.86–2.04 (2H, m), 3.52–3.66 (2H, m), 3.69–3.80 (1H, m), 3.86 (2H, s), 5.34 (1H, s), 6.81–6.96 (4H, m), 7.17–7.28 (4H, m).

EXAMPLE 7

(±)-Threo-3,4-dihydro-6-(1-hydroxy-2-(1-(4-hydroxy-4-phenoxymethyl)piperidinyl)propyl)quinolin-2(1H)one A total of 1.50 g (39.5 umol) of NaBH$_4$ was added portionwise to a suspension of 700 mg (1.71 mmol) of (±)-1-(5-(2-hydroxybenzimidazolyl))-2-(1-(4-hydroxy-4-phenoxymethyl)piperidinyl)propan-1-one in 20 mL of absolute ethanol and the reaction mixture was stirred overnight at room temperature. The solvent was then evaporated and the residual foam was taken up between ethyl acetate and water and the aqueous layer was extracted with ethyl acetate. The combined extracts were dried and evaporated and the residual foam was chromatographed on silica gel using 1:1 ethanol/ethyl acetate to give the product as a white solid, m.p. 192–196° C. A small amount of the erythro compound was formed in this reduction and could be separated from the column. NMR (CD$_3$OD) $\delta$ 0.82 (3H, d, J=7), 1.72–2.06 (4H, m), 2.50–2.82 (6H, m), 2.88–3.02 (2H, t, J=7), 3.02 (1H, t, J=7), 3.84 (2H, s), 4.28 (1H, d, J=7), 6.80–7.34 (8H, m);

Anal. Calcd for C$_{22}$H$_{27}$N$_3$O$_4$.1.5 H$_2$O:C, 65.88; H, 7.60; N, 6.40. Found: C, 65.74; H, 7.09; N, 6.31.

EXAMPLE 8

(±)-Erythro-5-(1-hydroxy-2-(1-(4-hydroxy-4-phenoxymethyl) piperidinyl)propyl)oxindole A mixture of 0.5 g (2.05 mmol) of 4-hydroxy-4-phenoxymethyl)piperidine hydrochloride, 0.5 g (2.25 mmol) of 5-(2-chloropropionyl)oxindole and 1 ml (0.725 g, 7.18 mmol) triethylamine in 20 mL of acetonitrile was refluxed for 24 h. The solvent was then removed in vacuo and the residues were partitioned between ethyl acetate and water. The ethyl acetate layer was washed with water and brine and was dried over MgSO$_4$ and concentrated to yield the ketone as a tan foam which was used for the following reaction without further purification, 537 mg (66%).

A solution of 500 mg (1.26 mmol) of the ketone in 20 mL of ethanol was treated portionwise with 1.0 g (26.3 mmol) of NaBH$_4$ and the resulting mixture was stirred at room temperature for 24 h. The solvent was removed in vacuo and the residues were partitioned between ethyl acetate and water. The ethyl acetate layer was washed and dried with brine and MgSO$_4$ and then evaporated to dryness. The residues were chromatographed on silica gel using ethyl acetate and gradually increasing concentrations of ethanol to give the threo product in pure fractions, 121 mg (24%), m.p. 204–207° C. NMR (DMSO-d$_6$) $\delta$ 0.70 (3H, d, J=7), 1.58–1.92 (4H, m), 2.40–2.65 (4H, m), 2.86 (1H, m), 3.32–3.40 (2H, m), 3.79 (2H, s), 4.20 (1H, d, J=7), 6.70–7.35 (8H, m), 10.34 (1H, s).

EXAMPLE 9

(±)-1-(6-(1,2,3,4-Tetrahydro-2-oxoquinolinyl))-2-(1-(4-hydroxy-4-phenoxymethyl)piperidinyl)propan-1-one A suspension of 8.30 g (34.06 mmol) of 4-hydroxy-4-phenoxymethylpiperidine hydrochloride and 8.09 g (34.06 mmol) of 6-(2-chloro-1-propionyl)-1,2,3,4-tetrahydroquinolin-2(1H)-one in 100 mL of acetonitrile was treated with 16.61 mL (12.04 g, 0.12 mol) of triethylamine and the mixture was heated at reflux for 3 h and then stirred overnight at room temperature.

The reaction mixture was poured into water and extracted 3 times with ethyl acetate and the combined extracts were dried with brine solution and magnesium sulfate and evaporated to give a foam. This foam was dissolved in hot methanol and ethyl acetate and cooled to give a tan solid which was found to be starting chloroketone and discarded. The filtrates were evaporated and dissolved in ethyl acetate and ether was added to facilitate crystallization. The product was filtered and washed with ether to give 8.84 g (63.6.%) of the product as a cream-colored solid, m.p. 137–139° C. The analytical sample was crystallized from hot ethyl acetate. NMR (CD$_3$OD) δ 1.28 (3H, d, J=7), 1.60–1.92 (4H, m), 2.52–2.84 (6H, m), 3.00 (2H, t, J=7), 3.75 (2H, s), 4.22 (1H, q, J=7), 6.82–7.00 (4H, m), 7.16 (2H, m), 7.82–7.98 (2H, m);

Anal. Calcd for C$_{24}$H$_{28}$N$_2$O$_4$:C, 70.56; H, 6.91; N, 6.86. Found: C, 70.16; H, 6.78; N, 6.76.

EXAMPLE 10

(±)-1-(5-(2-Hydroxybenzimidazolyl))-2-(1-(4-hydroxy-4-phenoxymethyl)piperidinyl)propan-1-one A suspension of 2.43 g (10.0 mol of 4-hydroxy-4-phenoxymethylpiperidine hydrochloride and 2.25 g (10.0 mmol) of 5-(2-chloro-1-propionyl)-2-hydroxybenzimidazole in 40 mL of acetonitrile was treated with 4.88 mL (3.53 g, 35.0 mmol) of triethylamine and the reaction mixture was heated at reflux for 90 min and then let sit over a weekend at room temperature.

The reaction mixture was then poured into a mixture of water and ethyl acetate and the resulting suspended solid was separated by filtration and found to be pure product, 1.15 g after drying. The filtrate was adjusted to pH=7.0 and extracted with ethyl acetate several times to give, after drying with brine solution and MgSO$_4$, a colorless solid which was recrystallized from hot ethyl acetate/methanol to give an additional 560 mg of product (total yield, 43%), m.p. 230–235° C. (dec.). NMR (CD$_3$OD/DMSO-d$_6$) δ 1.29 (2H, d, J=7), 1.60–1.92 (4H, m), 2.54–2.84 (4H, m), 3.77 (2H, s), 4.26 (1H, q, J=7), 6.86–7.10 (6H, m), 7.75–7.92 (2H, m).

EXAMPLE 11

(±)-1-(5-(Oxindolyl))-2-(1-(4-hydroxy-4-phenoxymethyl) piperidinyl)propan-1-one

Following the procedure of preparation 10, the present title compound was obtained from 4-hydroxy-4-phenoxymethylpiperidine hydrochloride (10.0 mmol), 5-(2-chloropropionyl)oxindole (10 mmol) and triethylamine (35 mmol) in 50 ml of acetonitrile. The title compound was isolated by crystallization from hot ethyl acetate/methanol to give an amorphous foam. Yield 66.4%. NMR (CDCl$_3$) δ 1.28 (3H, d, J=7), 1.58–1.78 (4H, m), 2.40–2.84 (4H, m), 3.54 (2H, s), 3.76 (2H, s), 4.09 (1H, q, J=7), 6.78–6.96 (3H, m), 7.14–7.26 (2H, m), 7.84–8.05 (3H, m), 9.52 (1H, broad s), 9.64 (1H, broad s).

Preparation 1
3,4 Dihydroquinolin-2-(1H)-one

A slurry of 50.0 g (0.259 mol) of o-nitrocinnamic acid in 500 mL of ethanol was treated with 5 teaspoons of Raney Ni and hydrogenated on a Parr shaker overnight at an initial pressure of 50 psi. In the morning, the pressure was increased again to 50 psi and the reaction was continued for an additional 5 h. The reaction mixture was filtered to remove the catalyst and then washed through a bed of silica gel with a mixture of ethyl acetate and ethanol to remove traces of nickel salts. Evaporation of the filtrate gave the desired product in 57% yield. NMR (DMSO-d$_6$) δ 2.45 (2H, t, J=7), 2.87 (2H, t, J=7), 6.87 (2H, d of d, J=7, 7), 7.12 (2H, d of d, J=7, 10), 10.08 (1H, s). m.p. 165–166° C.

Preparation 2
6-(2-Chloropropionyl)-3,4-dihydroquinolin-2-(1H) -one

A suspension of 72.5 g (0.544 mol) of AlCl$_3$ in 800 mL of CS$_2$ was stirred under dry N$_2$ while 14.1 mL (20.0 g, 0.177 mol) of 2-chloropropionyl chloride was added followed by 20.0 g (0.136 mol) of 3,4-dihydroquinolin-2(1H)-one. The reaction mixture was refluxed for 4 h at which time a separation of phases was noted. The reaction was quenched by pouring onto ice with vigorous stirring. The pale yellow precipitate which formed was separated by filtration, washed with water and dried overnight over P$_2$O$_5$ to give 27.7 g (91%) of the desired product, m.p. 236.5–238° C.

Preparation 3
5-(2-Chloropropionyl)-2-hydroxybenzimidazole

Following the procedure of Preparation 2, the present title compound was obtained from 2-hydroxybenzimidazole (0.136 mol), aluminum chloride (0.544 mol) and 2-chloropropionyl chloride (0.177 mol) in 800 ml CS$_2$. The title compound was isolated by filtration. Yield 92%, m.p. 245° dec.

Anal. Calcd for C$_{10}$H$_9$ClN$_2$O$_2$: C, 53.47; H, 4.04; N, 12.47. Found C, 54.41; H, 4.07; N, 13.25.

Preparation 4
5-(2-Chloropropionyl)oxindole

Following the procedure of Preparation 2, the present title compound was obtained from oxindole (0.136 mol), aluminum chloride (0.544 mol) and 2-chloropropionyl chloride (0.177 mol) in 800 ml CS$_2$. The title compound was isolated by filtration. Yield 91%, m.p. 157–158° C.

Preparation 5
6-(2-Chloroacetyl)-3,4-dihydroquinolin-2(1H)-one

Following the procedure of Preparation 2, the present title compound was obtained from 3,4-dihydroquinolin-2-(1H)-one (0.136 mol), aluminum chloride (0.544 mol) and 2-chloroacetyl chloride (0.177 mol) in 800 ml CS$_2$. The title compound was isolated by filtration. Yield 50%, m.p. 215–216° C.

Preparation 6
5-(2-Chloroacetyl)-2-hydroxybenzimidazole

Following the procedure of Preparation 2, the present title compound was obtained from 2-hydroxybenzimidazole (0.13.6 ol), aluminum chloride (0.544 ol) and 2-chloroacetyl chloride (0.177 mol) in 800 ml CS$_2$. The title compound was isolated by filtration. Quantitative yield, m.p. 273–275° C. (dec).

Preparation 7
5-(2-Chloroacetyl)-oxindole

Following the procedure of Preparation 2, the present title compound was obtained from oxindole (0.136 mol), aluminum chloride (0.544 mol) and 2-chloroacetyl chloride (0.177 mol) in 800 ml CS$_2$. The title compound was isolated by filtration. Yield 90%, m.p. 236.5–239° C.

Preparation 8
4 -fydroxy-4–2henoxymethylpiperidine hydrochloride

Oil free sodium hydride (2.16 g, 0.09 M) was added to dry dimethyl sulfoxide (250 mL) under nitrogen gas and the mixture was heated to 60–65° C. until a uniform black solution was formed, about 1 h. Then 19.83 g (0.09 M) of trimethylsulfoxonium iodide was added (slight exotherm) and the mixture was stirred until a brown solution occurred, about 30 min. Then a solution of 13.40 g (67.3 mM) of N-t-butyloxycarbonyl-4-piperidone in 50 mL of dimethyl sulfoxide was stirred at room temperature for 1 h. The reaction mixture was then poured into 1 L of cold water and the whole was extracted 4× with 100 mL portions of hexane. The combined hexane extracts was back-washed with 50 mL of water and with brine solution and was dried with magnesium sulfate, filtered and evaporated to give 11.75 g of white crystalline product, 6-t-butyloxycarbonyl-1-oxa-6-azaspiro[2.5]octane, (78% yield).

Further extraction of the aqueous layers with 3×50 mL of hexane gave a further 650 mg of product for a total yield of 82.5%.

m.p. 57.5–59.5° C.; IR(KBr) 5.90 μm; NMR δ 1.32–1.48 (2H, m), 1.42 (9H, s), 1.74–1.80 (2H, m), 2.65 (2H, s), 3.31–3.43 (2H, m), 3.61–3.72 (2H, m);

Anal. Calcd for $C_{11}H_{19}NO_3$: C, 61.94; H, 8.98; N, 6.57. Found: C, 62.05; H, 9.09; N, 6.58.

A solution of 10.37 g (0.11 M) of phenol in 100 mL of dry dimethyl sulfoxide treated portionwise with 1.99 g (82.8 mmol) of oil-free sodium hydride keeping the temperature between 20–25° C. with a cold water bath. The reaction mixture was then stirred at room temperature for 45 min to give a grey suspension. The 11.75 g (55.2 mmol) of 6-t-butyloxycarbonyl-1-oxa-6-azaspiro[2.5]octane dissolved in 65 mL of dimethyl sulfoxide was added dropwise after which the reaction mixture was heated to 55–60° C. for 7 h and was then stirred at room temperature overnight.

The reaction mixture was then poured into 1 L of cold water and extracted 4× with ether. The combined ether extracts was backwashed with 10% NaOH and with brine and was dried with magnesium sulfate evaporated to give the desired product, N-t-butyloxycarbonyl-4-hydroxy-4-phenoxymethylpiperidine, as an oil weighing 17.01 g (100%).

IR (Film) 5.91, 2.95 μM; NMR ($CDCl_3$) δ 1.46 (9H, s); 1.53–1.80 (4H, m), 3.13–3.30 (2H, m), 3.80 (2H, s), 3.80–3.98 (2H, m), 6.84–6.99 (2H, m), 7.22–7.44 (3H, m);

Anal. Calcd for $C_{17}H_{25}NO_4$: C, 66.42; H, 8.20; N, 4.56. Found: C, 65.72; H, 8.21; N, 4.77.

A solution of 17.0 g (0.055 M) of N-t-Butyloxycarbonyl-4-hydroxy-4-phenoxymethylpiperidine in 150 mL of methanol was saturated with HCl gas. After the mixture had cooled, it was again treated with HCl gas and this procedure was again repeated. After crystals had formed, the reaction mixture was treated with 500 mL of anhydrous ether and let stir at room temperature overnight.

The product was filtered and washed with dry ether and dried under a stream of dry $N_2$ to give 10.85 g (80.6%) of crystalline material, m.p. 202–204° C. IR (KBr) 3.06, 3.14, 3.44, 3.57, 3.56, 6.33, 8.06 μm; NMR ($D_2O$) δ 2.00 (4 H, broad s), 3.34 (4H, broad s), 4.00 (2H, s), 6.98–7.09 (3H, m), 7.30–7.43 (2H, m).

Anal. Calcd for $C_{12}H_{17}NO_2 \cdot HCl$: C, 59.13; H, 7.44; N, 5.75. Found: C, 58.98; H, 7.11; N, 5.65.

I claim:
1. A compound of the formula:

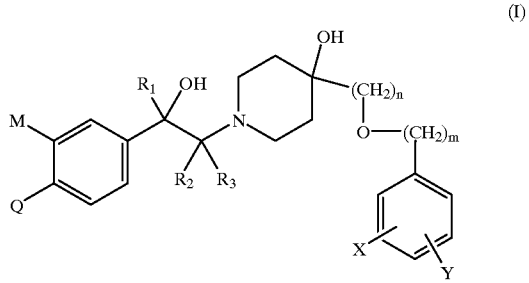

and the pharmaceutically-acceptable salts thereof; wherein $R_1$, $R_2$ and $R_3$ are each selected from the group consisting of hydrogen, alkyl having 1 to 6 carbons, phenyl and substituted phenyl, wherein the substituent on said substituted phenyl is selected from the group consisting of hydroxy, alkyl having 1 to 4 carbons, chloro, bromo, fluoro, trifouoromethyl, amino, nitro and alkoxy having 1 to 4 carbons;
or $R_1$ and $R_2$ when taken together to form a methylene, ethylene, propylene or butylene group;
m is o to 2;
n is 1 or 2;
X and Y are each selected from the group consisting of hydrogen, chloro, bromo, fluoro, trifluoromethyl, alkoxy having 1 to 4 carbons, alkyl having 1 to 4 carbons, hydroxy, amino, nitro and substituted phenoxy, wherein the substituent on said substituted phenoxy is selected from the group consisting of hydrogen, hydroxy, alkyl having 1 to 4 carbons, chloro, bromo, fluoro, trifluoromethyl, nitro, amino and alkoxy having 1 to 4 carbons;
M and Q are taken together and form a divalent radical Z, wherein Z is

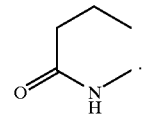

2. A compound according to claim 1, wherein $R_2$ is hydrogen; and $R_3$ is hydrogen or methyl.
3. A compound according to claim 2, wherein n is 1 and m is 0.
4. A compound according to claim 3, wherein $R_1$ is hydrogen.
5. A compound according to claim 4, wherein $R_3$ is hydrogen.
6. A compound according to claim 5, wherein X and Y are each hydrogen.
7. A compound according to claim 4 of the formula

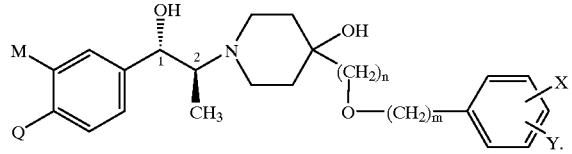

8. A compound according to claim 7, wherein X and Y are each hydrogen.

9. A compound according to claim 4 of the formula

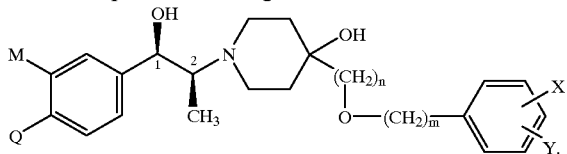

10. A compound according to claim 9, wherein X and Y are each hydrogen.

11. A pharmaceutical composition comprising a neuroprotective amount of a compound of claim 1 and a pharmaceutically acceptable carrier.

12. A method of treating traumatic injury to the brain and spinal cord, stroke or a CNS degenerative disease in a human subject which comprises administering to said human subject a neuroprotective amount of a compound of claim 1.

* * * * *